United States Patent [19]
Eckert et al.

[11] Patent Number: 5,247,556
[45] Date of Patent: Sep. 21, 1993

[54] METHOD AND APPARATUS OF OPERATING A COMPUTER TOMOGRAPHY APPARATUS TO SIMULTANEOUSLY OBTAIN AN X-RAY SHADOWGRAPH AND A TOMOGRAPHIC EXPOSURE

[75] Inventors: Rudolf Eckert, Spardorf; Willi Kalender, Kleinseebach, both of Fed. Rep. of Germany

[73] Assignee: Siemens Aktiengesellschaft, Munich, Fed. Rep. of Germany

[21] Appl. No.: 827,424

[22] Filed: Jan. 29, 1992

[30] Foreign Application Priority Data

Feb. 6, 1991 [DE] Fed. Rep. of Germany ....... 4103588

[51] Int. Cl.⁵ ............................................. H05G 1/64
[52] U.S. Cl. ...................................... 378/4; 378/99; 378/21; 358/111
[58] Field of Search ................... 378/4, 20, 21, 22, 23, 378/15, 24, 25, 98, 99, 189; 358/111

[56] References Cited

U.S. PATENT DOCUMENTS

| | | | |
|---|---|---|---|
| 4,174,481 | 11/1979 | Liebetruth | 378/4 |
| 4,352,986 | 10/1982 | Pfeiler | 378/14 |
| 5,103,469 | 4/1992 | Tanaka | 378/20 |

FOREIGN PATENT DOCUMENTS 2804732 1/1985 Fed. Rep. of Germany .
8703190.6 2/1987 Fed. Rep. of Germany .

Primary Examiner—David P. Porta
Assistant Examiner—Don Wong
Attorney, Agent, or Firm—Hill, Steadman & Simpson

[57] ABSTRACT

A computer tomography apparatus has an x-ray source and a radiation detector which permit a patient to be helically scanned to obtain a tomogram of the patient. Since it is frequently desirable to obtain a conventional x-ray image (shadowgraph) of the patient as well, a method is disclosed which permits the computer used to generate the tomogram to calculate such a shadowgraph of the patient from the data acquired for the tomogram, for desired projection directions. This data is acquired, and the shadowgraph obtained, simultaneously with the exposure used to produce the tomogram.

8 Claims, 3 Drawing Sheets

200000
METHOD AND APPARATUS OF OPERATING A COMPUTER TOMOGRAPHY APPARATUS TO SIMULTANEOUSLY OBTAIN AN X-RAY SHADOWGRAPH AND A TOMOGRAPHIC EXPOSURE

BACKGROUND OF THE INVENTION

1. Field of the Invention

The present invention is directed to a computer tomography apparatus of the type which undertakes a helical scan of an examination subject.

2. Description of the Prior Art

It is known in conventional computer tomography systems to produce a conventional x-ray image (shadowgraph) of an examination subject, for the purpose of defining the examination region before beginning the computer tomographic examination. For this purpose, the patient is usually moved through the measurement opening, with the x-ray focus being held at a fixed angular position, and a conventional shadowgraph, i.e., an x-ray projection image, is produced continuously, or pulsed line-by-line. This known technique of obtaining a conventional x-ray image using a computer tomography apparatus has several disadvantages. First, in addition to offering the standard computer tomographic exposure mode with continuous scanning, a further exposure mode must be offered wherein the x-ray focus is held stationary. Additionally, as a result of the creation of two separate exposures, the time required for the complete examination is higher by several minutes compared to the time needed for the actual production of the computer tomogram. Such lengthening of the exposure time is not only economically undesirable, but also the patient frequently changes position between the two exposures, so that a shifting between the selected body region and the body region which is actually registered during the examination can occur.

SUMMARY OF THE INVENTION

It is an object of the present invention to provide a computer tomography apparatus and method for operating such an apparatus which permit the simultaneous production of computer tomograms and x-ray shadowgraphs.

The object is achieved in a method for operating a computer tomography apparatus which has a measurement system for continuous (usually helical) scanning of a measurement volume in the direction of a central axis, wherein the computer calculates a shadowgraph of the patient from the tomographic data, the shadowgraph being calculated for a defined projection direction simultaneously with the tomography exposure. The exposure volume can thus be monitored in real time, and the exposure can be stopped when the end point, which can only be radiologically recognized, is reached. All of the data for three-dimensional reproduction of the volume in which the patient is situated are present after a helical scanning of the volume. Computer tomograms and shadowgraphs for arbitrary projection directions can therefore be reconstructed from such data.

DESCRIPTION OF THE PREFERRED EMBODIMENTS

Figure 1:
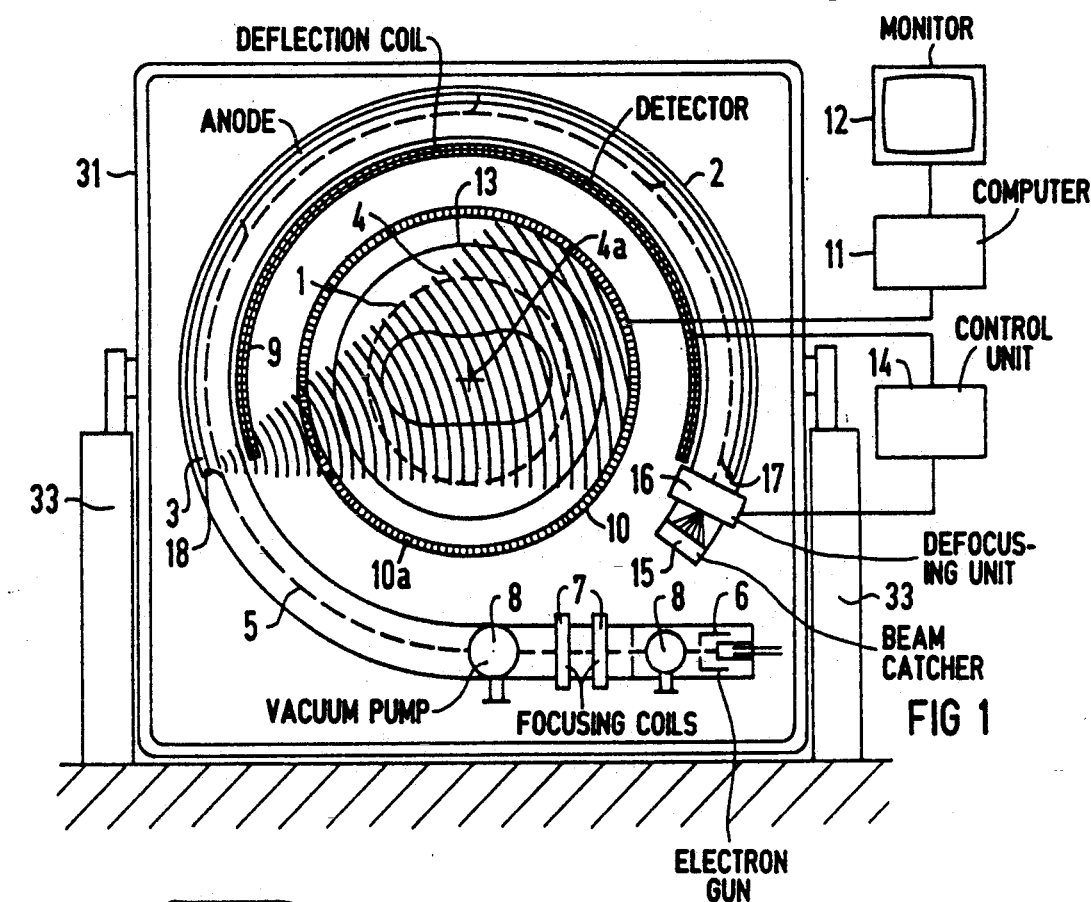
FIG. 1 is an end view of a computer tomography apparatus operable in accordance with the principles of the present invention, with the measurement system being vertically oriented and with certain electronic components being schematically indicated.
Figure 2:
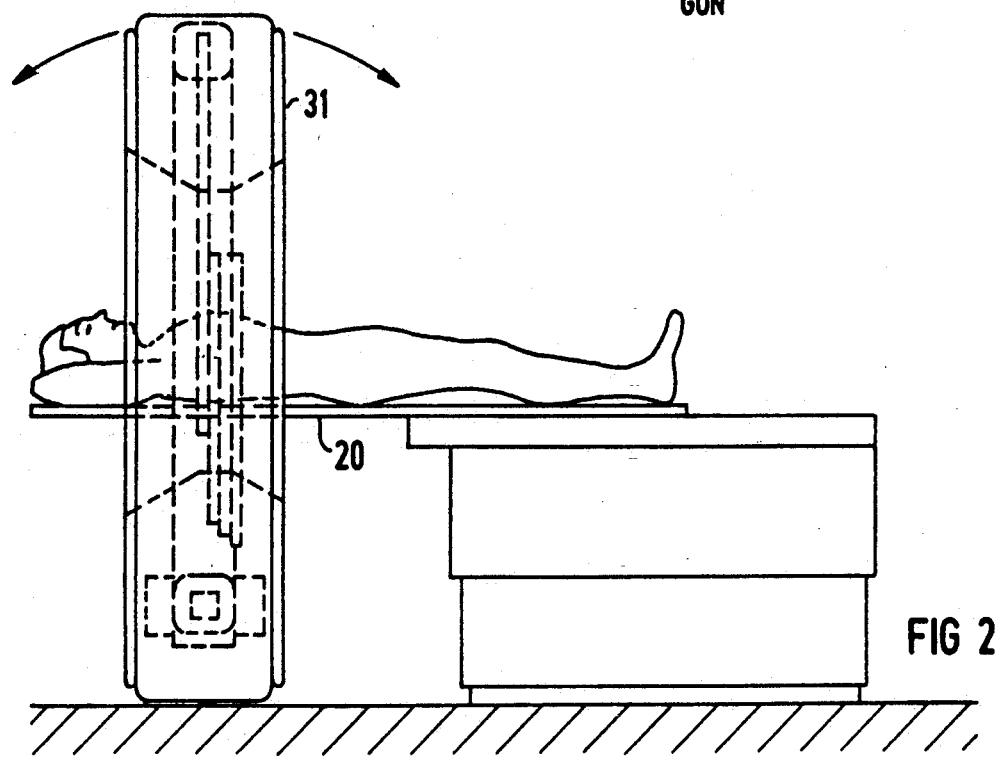
FIG. 2 is a side view of the computer tomography apparatus of FIG. 1.

An x-ray computer tomography apparatus operable in accordance with the principles of the present invention is shown in FIG. 1 having a measurement system 31 which, in FIGS. 1 and 2 is shown oriented vertically. The measurement system 31 has a housing surrounding a measurement field 1, with an x-ray source 2 and an annular anode 3 disposed in the housing. For producing a rotating, fan-shaped x-ray beam 4, the annular anode 3 is scanned by an electron beam 5 which is produced by an electron gun 6. The electron gun 6 is followed by focusing coils 7. A vacuum is maintained in the x-ray source 2 by vacuum pumps 8.

The electron beam is deflected onto the annular anode 3 by a magnetic deflection coil 9 for producing the x-ray beam 4. The x-rays emerging from the examination subject situated in the measurement field 1 are acquired by an annular radiation detector 10, consisting of a series of detector elements 10a. The respective output signals of the detector elements 10a are supplied to a computer 11, which calculates an image of the examined slice of the examination subject from those signals. The image is visually displayed on a monitor 12.

The measurement field 1 is a field in an opening 13 in the housing of the measurement system 31, through which the examination subject is moved. For transirradiation of the examination subject from different directions, the x-ray beam 4 rotates around an axis 4a by deflection of the electron beam 5 on the annular anode 3.

A control unit 14 operates the deflection coil 9 so that the electron beam 5 penetrates the x-ray source 2 concentrically relative to the annular anode 3 before the beginning of a scan event, until the electron beam 5 is incident on a beam catcher 15 at the closed end. The beam catcher 15 may consist, for example, of lead. Prior to reaching the beam catcher 15, the electron beam 5 is defocussed by a defocussing unit 16.

The electron beam 5 is then deflected onto the annular anode 3 by the deflection coil 9, and scans the annular anode 3 from its end 17 to its end 18. Five focus positions are shown in FIG. 1, however, there are significantly more discrete focus positions, for example one thousand. Preferably, however, the focus is continually shifted by a traveling wave, so that scanning is defined by the detector sampling. The x-ray beam 4 thus rotates in a direction opposite to the direction of the electron beam 5, and is shown in its final position in FIG. 1, at which point the scan event is terminated.

Another deflection of the annularly guided electron beam 5 subsequently takes place, with a new scan event beginning with the deflection of the electron beam 5 onto the end 17 of the annular anode 3.

It is also possible to scan the annular anode 3 with an electron beam 5 moving in the clockwise direction, i.e., from the end 18 to the end 17 of the annular anode 3.

The radiation detector 10 is disposed relative to the annular anode 3 so that the x-ray beam 4 can pass by the detector 10 before the beam 4 enters the measurement field 1. The x-ray beam 4 is incident on the radiation detector 10 only after emerging from the measurement field 1.

Figure 3:
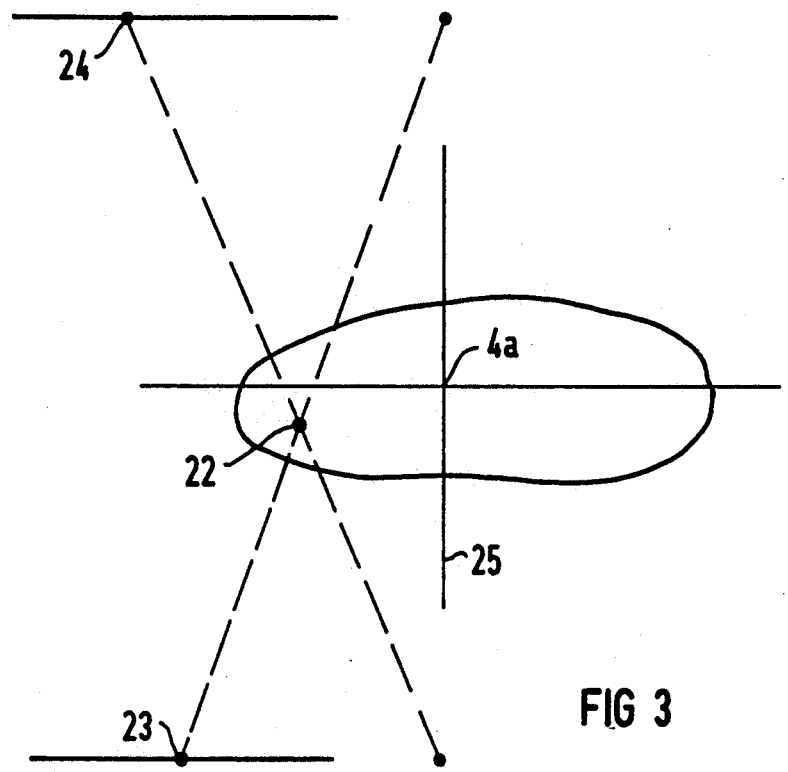
FIGS. 3 and 4 are graphs for explaining the production of x-ray shadowgraphs in the computer tomography apparatus of FIGS. 1 and 2, in accordance with the principles of the present invention.

As can be seen in FIG. 2, a patient on a support 20 is moved through the measurement field 1 while the beam focus is rotated on the annular anode 3. A defined measurement volume of the patient is thus helically scanned, or is scanned over a portion of a helix. From the data acquired thereby, the computer 11 can calculate both tomograms for predetermined transverse slices of the patient and shadowgraphs (conventional x-ray images) for defined projection angles. The particular projection angle can be selectable. A shadowgraph should preferably be produced in lateral and anterior-posterior projection. In order to double the number of image lines in the shadowgraph, the data from projections from focus positions offset by 180° can be used. Except for the central ray and at the level of the rotational center, these projections in fan geometry will result in portions of the image being projected onto different detector positions, therefore, some deterioration in the image quality must be expected. This can be seen in FIG. 3, wherein the patient is shown in cross section. Details of the examination subject image outside of the rotational center (axis 4a), for example the detail 22, are projected onto different points in the image plane, given a fan-beam projection from opposite directions, as can be seen, for example, with respect to points 23 and 24 which have different spacings from the axis 25.

Figure 4:
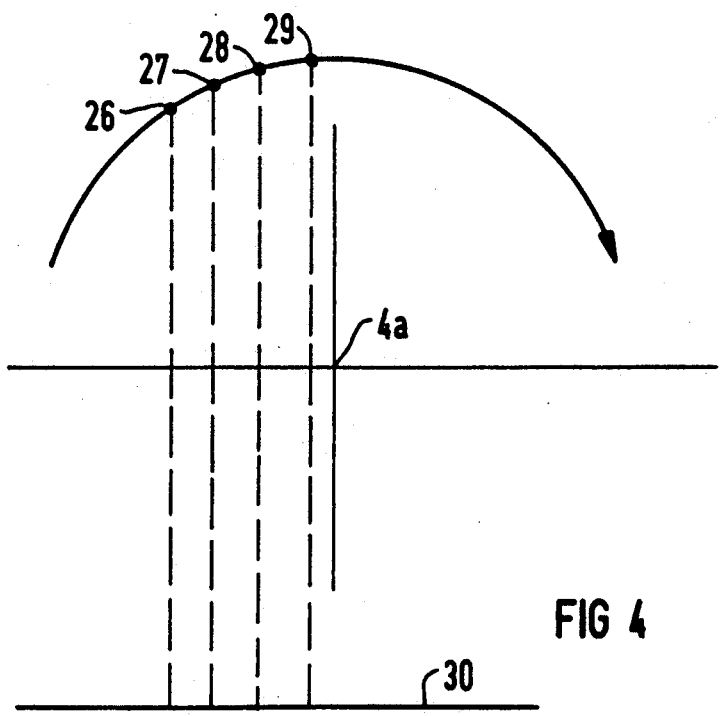

To avoid these disadvantages, data corresponding to parallel projections can be calculated from the data of the helical movement for arbitrary projection angles, as shown in FIG. 4.

Four focus positions 26, 27, 28 and 29 are shown in FIG. 4, with the associated parallel rays which are incident on the projection plane 30.

An image consequently arises after n revolutions of the focus, or 2 n measured lines. A calculation of additional image lines by interpolation is also possible.

Because a two-dimensional convolution is usually implemented to improve the image quality, the image for the region n−m (or 2 n−m) lines can be portrayed in so-called final quality, while the remaining region is portrayed in a preliminary processing condition, given a convolution core over a 2 m line range. Looking at this image, the attendant or physician can recognize when the desired examination region is scanned, and the helical exposure is to be aborted. This can be implemented manually, such as by a so-called dead man circuit.

The method disclosed herein can also be used in computer tomography systems having a measuring system of the type with a conventional x-ray tube and radiation detector, with means for mechanically rotating these components around an axis. The method can be used to particular advantage, however, in a system of the type described above with an annular anode, because such systems do not require pauses for cooling, due to limited x-ray power, and thus helical computer tomography exposures of larger volumes can be undertaken in a shorter time without interruption. The method is also particularly useful for conducting an examination of a standing patient wherein the time lost due to the generation of an additional shadowgraph is highly disadvantageous, because the patient, without a patient support, is more likely to move between exposures, and in some instances standing for a length of time may be difficult for certain patients.

Figure 5:
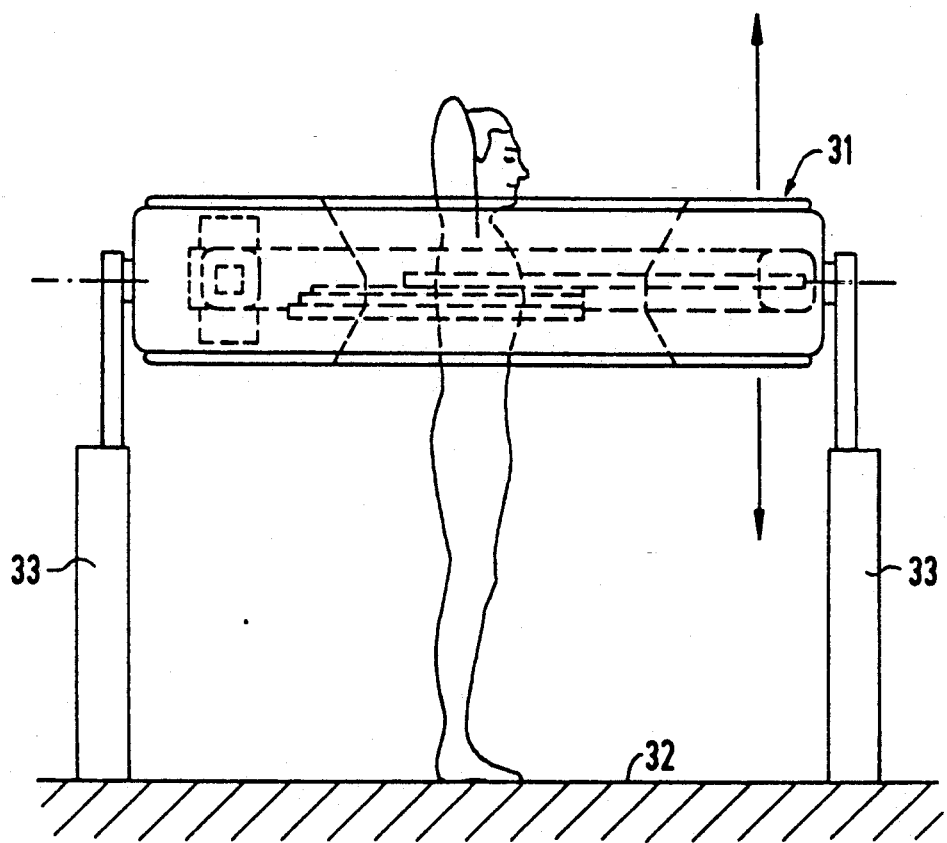
FIG. 5 is a side view of a further embodiment of a computer tomography apparatus operable in accordance with the principles of the present invention, with the measurement system horizontally oriented.

An arrangement of the computer tomography apparatus for conducting an examination of standing patient is shown in FIG. 5, with the measurement system 31 being horizontally oriented relative to a platform 32 on which the examination subject stands. The measurement system 31 is mounted on supports 33 so as to be height-adjustable in the vertical direction, as indicated by the double arrows. A helical exposure of a standing patient is thereby possible.

The image quality of the shadowgraph is adequate in all instances for computer tomography systems having annular anodes with which exposures of thin layers, possible with a multi-line detector are provided, and can even be superior to current shadowgraphs. Due to the prevention of parallax errors, the creation of the shadowgraphs from parallel projections constitutes a clear advantage over the conical projection used in conventional x-ray exposures, as well as in comparison to the cylindrical projection which is conventionally used to make a shadowgraph in a computer tomography apparatus.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computer tomography apparatus comprising:
   measurement means for conducting a scan of a measurement volume around and along a central axis of said volume including an x-ray source which generates a fan-shaped x-ray beam propagating through said measurement volume at a plurality of different projection angles of said central axis and detector means for receiving x-rays after passing through said volume for generating image data;
   computer means for simultaneously calculating in real time a shadowgraph of a subject in said measurement volume from data for specific ones of said projection angles in said scan and for calculating a tomogram of said subject from data for all of said projection angles in said scan;
   means for monitoring said measurement volume real time for terminating said scan when a radiologically recognizable end point is reached; and
   means for displaying said shadowgraph and said tomogram.

2. A computer tomography apparatus as claimed in claim 1 wherein said computer means includes for means for selecting a projection angle for said shadowgraph.

3. A computer tomography apparatus as claimed in claim 1 wherein said computer means receives data for projections from positions of a focus of said x-ray beam which are offset by 180° for calculating said shadowgraph.

4. A computer tomography apparatus as claimed in claim 1 wherein said means for scanning is a means for helically scanning said measurement volume and wherein said computer means uses data from a plurality of parallel projections acquired during said helical scanning for calculating said shadowgraph.

5. A method for operating a computer tomography apparatus comprising the steps of:
 conducting a scan of a measurement volume by continuously scanning said measurement volume around and along a central axis of said measurement volume by directing a fan-shaped x-ray beam at an examination subject in said measurement volume at a plurality of different projection angles of said central axis and acquiring data in the form of electrical signals corresponding to radiation attenuated by said subject;
 calculating a tomogram of said examination subject in real time from said data during a scan;
 calculating a shadowgraph of said examination subject during said scan from specific ones of said projection angles in said data simultaneously with calculating said tomogram;
 monitoring said tomogram exposure in real time and terminating said exposure when a radiologically recognizable end point is reached; and
 displaying said shadowgraph and said tomogram.

6. A method as claimed in claim 5 comprising the additional step of selecting a projection angle for said shadowgraph.

7. A method as claimed in claim 5 comprising the additional step of: using data corresponding to projections from x-ray focus positions which are offset by 180° in the calculation of said shadowgraph.

8. A method as claimed in claim 5 wherein the step of continuously scanning is further defined by continuously helically scanning said measurement volume, and comprising the additional step of acquiring data from a plurality of parallel projections of said examination subject.

* * * * *